United States Patent [19]

Junge et al.

[11] 4,312,872

[45] Jan. 26, 1982

[54] 1-ALKA-2,4-DIENYL-2-HYDROXYMETHYL-3,4,5-TRIHYDROXYPIPERIDINES AS INHIBITORS OF α-GLUCOSIDE HYDROLASES

[75] Inventors: Bodo Junge; Lutz Müller; Rüdiger Sitt; Günter Thomas; Hans P. Krause; Walter Puls, all of Wuppertal, Fed. Rep. of Germany

[73] Assignee: Bayer Aktiengesellschaft, Leverkusen, Fed. Rep. of Germany

[21] Appl. No.: 158,541

[22] Filed: Jun. 11, 1980

[30] Foreign Application Priority Data

Jun. 27, 1979 [DE] Fed. Rep. of Germany ....... 2925943

[51] Int. Cl.³ ................ A61K 31/445; C07D 211/146
[52] U.S. Cl. ..................................... 424/267; 546/242
[58] Field of Search ......................... 546/242; 424/267

[56] References Cited

U.S. PATENT DOCUMENTS 4,182,767  1/1980  Murai et al. ..................... 546/242

OTHER PUBLICATIONS

March, J., *Advanced Organic Chemistry*, McGraw Hill, New York, 1968, pp. 331, 668 and 669.

*Primary Examiner*—Richard A. Schwartz
*Attorney, Agent, or Firm*—Sprung, Felfe, Horn, Lynch & Kramer

[57] ABSTRACT

The invention relates to 1-alka-2,4-dienyl-2-hydroxymethyl-3,4,5-trihydroxypiperidine compounds which are, inter alia, potent inhibitors for α- glucoside hydrolases and effect lipid absorption. Also included in the invention are methods for the manufacture of the said compounds, compositions containing said compounds and methods for the use of said compounds and compositions.

10 Claims, No Drawings

1-ALKA-2,4-DIENYL-2-HYDROXYMETHYL-3,4,5-TRIHYDROXYPIPERIDINES AS INHIBITORS OF α-GLUCOSIDE HYDROLASES

The present invention relates to new 2-hydroxymethyl-3,4,5-trihydroxypiperidine compounds, to processes for their production and to their use as medicaments, in particular against diabetes, hyperlipoproteinaemia, atherosclerosis and adiposity.

It has already been disclosed that N-alkyl derivatives and N-alkenyl derivatives of 2-hydroxymethyl-3,4,5-trihydroxypiperidine are potent inhibitors for α-glucoside hydrolases. Furthermore, it has been disclosed that N-alkyl derivatives of these compounds with alkyl radicals of average chain length ($C_5$ to $C_{14}$) inhibit absorption of lipids from the intestines (South African patent application No. 78/4843). However, compared with 1-methyl-2-hydroxymethyl-3,4,5-trihydroxypiperidine, the compounds last mentioned have a reduced effect on α-glucoside hydrolases.

According to the present invention there are provided compounds which are 2-hydroxy-methyl-3,4,5-trihydroxypiperidine derivatives of the general formula

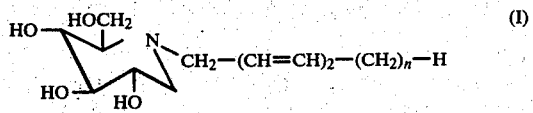

in the form of individual stereoisomers or mixtures thereof, in which n is 0, 1, 2, 3, 4 or 5. The compounds of the present invention combine a maximum effect on α-glucoside hydrolases and on lipid absorption.

According to the present invention there is further provided a process for the production of compounds of the invention in which (a) 2-hydroxymethyl-3,4,5-trihydroxypiperidine (1-desoxynojirimicin) is subjected to reductive alkylation with an aldehyde of the general formula $$OCH-(CH=CH)_2-(CH_2)_n-H \quad (II)$$

in which n is 0, 1, 2, 3, 4 or 5,
in the presence of a hydrogen donor, or (b) 1-desoxynojirimicin is reacted with an alkyl halide of the general formula $$X-CH_2-(CH=CH)_2-(CH_2)_n-H \quad (III)$$

in which
n has the meaning indicated above and
X denotes a halogen atom, preferably a chlorine, bromine or iodine atom.

By way of illustration of reaction variant (a), if 1-desoxynojirimicin is reacted with sorbic aldehyde and NaCNBH$_3$ as the hydrogen donor, the course of the reaction can be formulated as follows:

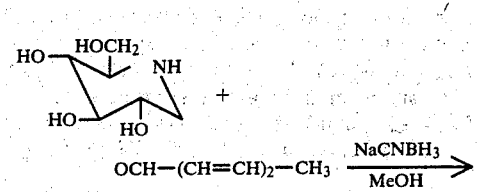

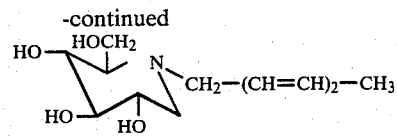

By way of illustration of reaction variant (b), if 1-desoxynojirimicin is reacted with 1-bromo-hexa-2,4-diene under the specified conditions, the reaction is shown by the following equation:

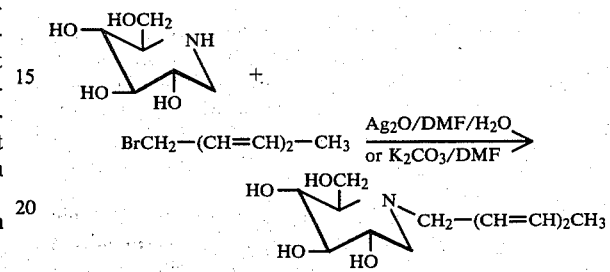

1-Desoxynojirimicin and the aldehydes of the formula (II) (E. L. Pippen u. M. Nonaka, J. Org. Chem. 23, 1580 (1958)) and halides of the formula (III) (M. Jacobson, J. Amer. Chem. Soc. 77, 2461 (1955)) are known from the literature, or they can be prepared by processes which are known from the literature.

Alkali metal cyanoborohydrides, dialkylaminoboranes and alkali metal borohydrides are preferred as hydrogen donor reducing agents for the reductive alkylation of reaction variant (a). It is particularly preferable to use sodium cyanoborohydride in this process variant. The reaction is preferably carried out at temperatures between −20° C. and room temperature. However, it can also be favourable to heat the mixture to the reflux temperature.

The process is preferably carried out in an inert solvent. Although anhydrous aprotic solvents can be employed (for example tetrahydrofurane if the reducing agent is morpholinoborane), a protic solvent is nevertheless usually used. A particularly suitable protic solvent is a $C_1$ to $C_6$ alkanol. However, water or an aqueous $C_1$ to $C_6$ alkanol (for example aqueous methanol or ethanol) or other aqueous solvent systems, such as, for example, aqueous dimethylformamide, aqueous hexamethylphosphoric acid triamide, aqueous tetrahydrofurane or aqueous ethylene glycol dimethyl ether, can also be used.

The process is preferably carried out in a pH range of 1 to 11, and a pH range of between 4 and 7 is particularly preferred.

The reaction variant (b) is preferably carried out in polar, protic or aprotic solvents, preferably in the presence of an acid-binding agent, at temperatures between 0° C. and the boiling point of the solvent.

Acid-binding agents which are employed are, preferably alkali metal hydroxides, carbonates and bicarbonates and alkaline earth metal hydroxides, carbonates and bicarbonates, silver oxide, ammonia and amines, such as $C_1$-$C_6$-trialkylamines, for example triethylamine or pyridine.

The reaction is preferably carried out in dimethylformamide/water, with Ag$_2$O as the acid-binding agent, or dimethylformamide, with potassium carbonate as the acid-binding agent.

Active compounds which may be mentioned are N-hexa-2,4-dienyl-1-desoxynojirimicin, N-hepta-2,4-dienyl-1-desoxynojirimicin, N-octa-2,4-dienyl-1-desoxynojirimicin, N-nona-2,4-dienyl-1-desoxymojirimicin, N-deca-2,4-dienyl-1-desoxymojirimicin and N-penta-2,4-dienyl-1-desoxynojirimicin.

It should be pointed out that most of the active compounds mentioned comprise 4 stereoisomeric compounds with regard to the arrangement of the substituents on the two double bonds. The invention relates both to the individual stereoisomers and to mixtures thereof.

The inhibitors according to the invention are suitable as therapeutic agents for the following indications in warm-blooded animals: prediabetes, gastritis, constipation, caries, infections of the gastrointestinal tract, meteorism, flatulence, hypertension and, especially atherosclerosis, adiposity, diabetes and hyperlipoproteinaemia.

To broaden the action spectrum, it can be advisable to combine inhibitors for glycoside hydrolases which complement one another in their action, the combinations being either combinations of the inhibitors according to the invention with one another or combinations of the inhibitors according to the invention with inhibitors which are already known.

In some cases, it is advantageous to provide combinations of the inhibitors according to the invention with known oral antidiabetic agents ($\beta$-cytotropic sulphonylurea derivatives and/or biguanides having an action on the blood sugar), and with active compounds which lower the blood lipid level, such as, for example, clofibrate, nicotinic acid, cholestyramine and others.

As stated above, the invention also relates to the use in medicine of the compounds of the invention.

The present invention provides a pharmaceutical composition containing as active ingredient a compound of the invention in admixture with a solid, liquid of liquefied gaseous diluent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The compounds can be administered without dilution, for example as powders or in a gelatine casing, or in combination with an excipient in a pharmaceutical composition.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicaments according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for oral administration of the medicaments of the invention is 25 mg to 5 g of active ingredient.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

In general it has proved advantageous to administer orally amounts of from 0.5 mg to 100 mg/kg of body weight per day to achieve effective results. Nevertheless, it can at times be necessary to deviate from those dosage rates, and in particular to do so as a function of the nature and body weight of the subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The manner in which the compounds according to the invention are formulated and administered can be found in European published application No. 947 corresponding to U.S. application Ser. No. 936,280 filed Aug. 23, 1978.

In vitro saccharase inhibition test

The in vitro saccharase inhibition test makes it possible to determine the inhibitory activity of a substance on enzymes by comparing the activity of solubilised intestinal disaccharidase complex in the presence and in the absence (so-called 100% value) of the inhibitor. A virtually glucose-free sucrose (glucose >100 ppm) is used as the substrate which determines the specificity of the inhibition test; the determination of the enzyme activity is based on the spectrophotometric determination of glucose liberated by means of glucose dehydrogenase and nicotinamide-adenine dinucleotide as the cofactor.

A saccharase inhibitor unit (SIU) is defined as the inhibitory activity which reduces a given saccharolytic activity in a defined test batch by one unit (saccharase unit=SU); the saccharase unit is thereby defined as the enzyme activity which, under the given conditions, splits one $\mu$mol of sucrose per minute and thus leads to the liberation of one $\mu$mol each of glucose, which is determined in the test, and fructose, which is not recorded in the test.

The intestinal disaccharidase complex is obtained from swine small intestine mucosa by tryptic digestion, precipitation from 66% strength ethanol at $-20°$ C., taking up of the precipitate in 100 mM phosphate buffer of pH 7.0 and finally dialysis against the same buffer.

100 $\mu$l of a dilution of the intestinal disaccharidase complex in 0.1 M maleate buffer of pH 6.25 are added to 10 $\mu$l of a sample solution which is made up such that the extinction of the test batch is at least 10%, but not more than 25%, below that of the 100% value, and the mixture is pre-incubated at 37° C. for 10 minutes. The dilution of the disaccharidase complex is to be adjusted to an activity of 0.1 SU/ml.

The saccharolytic reaction is then started by adding 100 $\mu$l of a 0.4 M solution of sucrose ("SERVA 35579") in 0.1 M maleate buffer of pH 6.25 and, after an incubation period of 20 minutes at 37° C., is stopped by adding 1 ml of glucose dehydrogenase reagent (1 small bottle of a lyophilised glucose dehydrogenase/mutarotase mixture ("MERCK 14053") and 331.7 mg of $\beta$-nicotinamide-adenine dinucleotide (free acid, "BOEHRINGER," degree of purity I) dissolved in 250 ml of 0.5 M tris buffer of pH 7.6). To determine the glucose, the mixture is incubated at 37° C. for 30 minutes and finally measured photometrically at 340 nm against a reagent blank (with the enzyme but without sucrose).

Calculation of the inhibitory activity of inhibitors is made difficult by the fact that even slight changes in the test system, for example a 100% value which varies slightly from determination to determination, have an influence on the test result which can no longer be ignored. These difficulties are by-passed by running a standard with each determination; a saccharase inhibitor of the formula $C_{25}H_{42}O_{18}N$ which has a specific inhibitory activity of 77,700 SIU/g, and, when employed in the test in amounts of 10 to 20 ng, leads to an inhibition of the order of size specified above, is used as the standard. When the difference in the extinctions at 340 nm between the 100% value and the batch inhibited by the standard is known, it is possible to calculate the specific inhibitory activity of the inhibitor, expressed in saccharase inhibitor units per gram (SIU/g), in a known manner from the difference in extinction between the 100% value and the batch inhibited by the sample solution, taking into consideration the amount of inhibitor employed.

The following Examples illustrate the preparation of compounds of the present invention

EXAMPLE 1

N-Hexa-2,4-dienyl-1-desoxynojirimicin

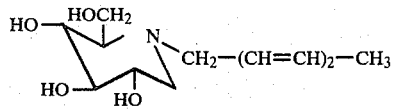

4.4 ml of hexadienal and 3 g of sodium cyanoborohydride are added to a solution of 5 g of 1-desoxynojirimicin in 100 ml of methanol and 4.5 ml of glacial acetic acid at 0° C. After stirring the mixture at 0° C. for one hour, it is stirred at room temperature for 18 hours.

The mixture is concentrated to dryness, the residue is taken up in water and the aqueous mixture is discharged onto a column 120 cm long and 3.5 cm wide, containing cellulose as the stationary phase and acetone as the mobile phase.

The column is first eluted with acetone and then with acetone to which water is added stepwise to the extent of 30%. The individual fractions are examined by thin layer chromatography and those containing the desired product are combined and concentrated.

After crystallisation of the residue with acetone, 4 g of the required compound are obtained, with a RF value of 0.55 (running agent: chloroform/methanol-/aqueous ammonia 4:3:1), RF value for 1-desoxynojirimicin: 0.21. Melting point: 172°–173° C.

EXAMPLE 2

The following compound was obtained analogously to Example 1 using corresponding starting materials.

N-hepta-2,4-dienyl-1-desoxynojirimicin

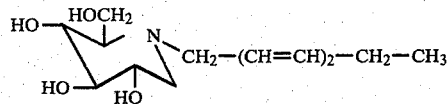

RF value: 0.57:
RF value for 1-desoxynojirimicin: 0.21
Melting point: 135°–137° C.

EXAMPLE 3

N-Hexa-2,4-dienyl-1-desoxynojirimicin

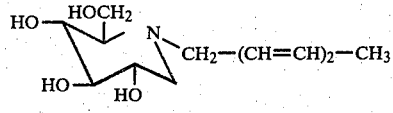

22 ml of hexadienal and 15 g of sodium cyanoborohydride are added to a solution of 25 g of 1-desoxynojirimicin in 500 ml of methanol and 22.5 ml of glacial acetic acid at 0° C. After stirring the mixture at 0° C. for one hour, it is stirred at room temperature for 18 hours.

The reaction mixture is then discharged onto a column packed with Amberlite IR 120 (H⊕ form) and the column is eluted first with alcohol/water 2:1 and then with alcohol/water 2:1 which contains 4% of NH$_3$. The ammoniacal eluate is concentrated to dryness and the residue is crystallised from acetone. The crystalline product is dissolved in water and the solution is discharged onto a column packed with Amberlite IR 400 (OH⊖ form). The column is eluted with alcohol/water 1:1 and the eluate is concentrated to dryness in a rotary evaporator. The residue is crystallised from a little water. Yield: 14.4 g of N-hexa-2,4-dienyl-1-desoxynojirimicin. Melting point: 172°–173° C.

EXAMPLE 4

Using the procedure of Example 1 except that an equivalent amount of pentadienal is substituted for the reference hexadienal, N-penta-2,4,-dienyl-1-desoxynojirimicin is obtained.

EXAMPLE 5

N-hexa-2,4-dienyl-1-desoxynojirimicin 130.4 g of 1-desoxynojirimicin and 154.8 g of finely powdered $K_2CO_3$ were stirred in 1.3 l of DMF (dimethyl formamide). 180.3 g of 1-bromo hexadiene-2,4 in 200 ml DMF were added at room temperature in one portion. The reaction temperature raised to 40° C. The mixture was stirred for 2 h at room temperature. The precipitated salts were filtered off with a suction filter and the filter cake was washed 2× with 50 ml DMF each. 2 l of ice water were added to the filtrate and the mixture was extracted 2× with 500 ml diethyl ether each. The water/DMF layer was then evaporated to dry under reduced pressure at about 50° C. The resulting residue was stirred with 1.4 l acetone and succeed off at 0° C. yielding 150.5 g of salt-containing raw material. The raw material was recrystallized from 200 ml of water. Yield 90 g of N-hexadienyl-1-desoxynojirimicin; m.p. 165°–168° C.

EXAMPLE 6

The product obtained according Example 3 is a mixture of two cis/trans isomers. According to HPLC and $H^1$—NMR investigation it contains 90 to 95% of the trans/trans compound

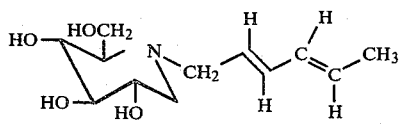

and 5 to 10% of the trans/cis compound

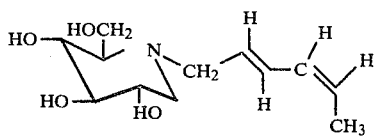

The two compounds were separated in 2325 separation stages with the Craig method (recycling method) in n-butanol/water 1:1. 615 mg of the trans/trans compound (purity >99.5% according to HPLC) and 50 mg of the trans/cis compound (purity >98%; (HPLC); m.p. 107°–110° C.) were obtained from 3.3 g starting material.

Both isomers were tested in vitro in the saccharase inhibiting test (described supra). The trans/trans isomer inhibits saccharase from swine small intestine mucosa 6× more than 1-desoxynojirimicin whereas the trans/cis isomer does 4×.

The present invention also comprises pharmaceutically acceptable bioprecursors of the active compounds of the present invention.

For the purpose of this specification the term 'pharmaceutically acceptable bioprecursors' of an active compound of the invention means a compound having a structural formula different from the active compound but which nonetheless, upon administration to a warm-blooded animal is converted in the patient's body to the active compound.

What is claimed is:

1. A 2-hydroxymethyl-3,4,5-trihydroxypiperidine derivative of the formula

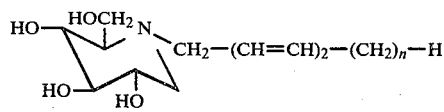

in the form of individual stereoisomers or mixtures thereof, in which n is 0, 1, 2, 3, 4 or 5.

2. A compound according to claim 1 in which n is 1, 2, 3, 4 or 5.

3. A compound according to claim 1 which is N-hexa-2,4-dienyl-1-desoxynijirimicin.

4. A compound according to claim 1 which is N-penta-2,4-dienyl-1-desoxynojirimicin.

5. A pharmaceutical composition containing as an active ingredient an amount effective for treating adiposity, diabetes or lipoproteinaemia, of a compound according to claim 1 in admixture with a solid, liquid or liquefied gaseous pharmaceutical diluent.

6. A composition according to claim 5 containing from 0.1 to 99.5% by weight of the said active ingredient.

7. A medicament in dosage unit form comprising an amount effective for treating adiposity, diabetes or lipoproteinaemia, of a compound according to claim 1 together with an inert pharmaceutical carrier.

8. A medicament of claim 7 in the form of tablets, pills, dragees, capsules, ampoules, or suppositories.

9. A method of combating adiposity, diabetes or lipoproteinaemia in warm-blooded animals which comprises administering to the animals an amount effective for treating adiposity, diabetes or lipoproteinaemia, of an active compound according to claim 1 either alone or in admixture with a pharmaceutical diluent or in the form of a medicament.

10. A method according to claim 9 in which the active compound is administered in an amount of 0.5 to 100 mg per kg body weight per day.

* * * * *